United States Patent [19]
Boury

[11] Patent Number: 5,911,725
[45] Date of Patent: Jun. 15, 1999

[54] INTRALUMINAL RETRIEVAL CATHETER

[76] Inventor: Harb N. Boury, 120 Sunset Ave., Glen Ellyn, Ill. 60137

[21] Appl. No.: 08/916,301

[22] Filed: Aug. 22, 1997

[51] Int. Cl.$^6$ ..................................................... A61F 11/00
[52] U.S. Cl. ........................................... 606/108; 606/194
[58] Field of Search ..................................... 606/110, 113, 606/114, 127, 128, 159, 108, 191–200, 205–208; 604/96–104, 19, 22

[56] References Cited

U.S. PATENT DOCUMENTS

| | | | |
|---|---|---|---|
| 5,387,219 | 2/1995 | Rappe | 606/108 |
| 5,460,610 | 10/1995 | Michael | 604/101 |
| 5,468,239 | 11/1995 | Tanner et al. | 604/101 |

FOREIGN PATENT DOCUMENTS

| | | | |
|---|---|---|---|
| 2577410 | 8/1986 | France | 604/101 |
| 1069823 | 11/1959 | Germany | 606/127 |

*Primary Examiner*—Glenn K. Dawson
*Attorney, Agent, or Firm*—Niro, Scavone, Haller & Niro

[57] ABSTRACT

An intraluminal retrieval device includes an outer catheter insertable by its distal end region into an artery or other body lumen that contains an unwanted object. The catheter supports two spaced apart expandable balloons, and is alignable to position the balloons on opposite sides of the object, whereupon the balloons when inflated secure the catheter and isolate a segment of the artery containing the object. The outer catheter includes at least one window between the balloons. An inner catheter is contained within the outer catheter and is movable relative to the outer catheter to alternatively open and close each window. With the outer catheter fixed in the artery and with the window open, a snare, vacuum or positive irrigation flow is used to retrieve the object by conveying it through the window into a retrieval chamber formed by the outer catheter either alone or in cooperation with the inner catheter. Outer catheters with several windows enable selective alignment of the catheters to choose a window nearest the object, or to choose from among windows of different sizes and shapes for closer correspondence to the object requiring retrieval. A smaller version of the device employs a single catheter with a retrieval opening between two microballoons for intracranial retrieval applications.

30 Claims, 3 Drawing Sheets

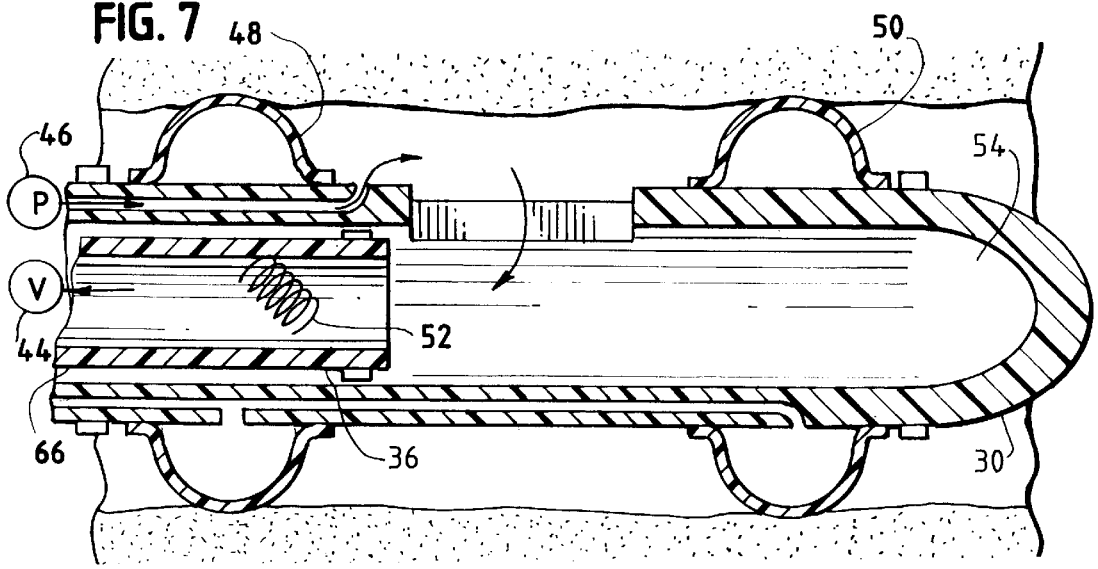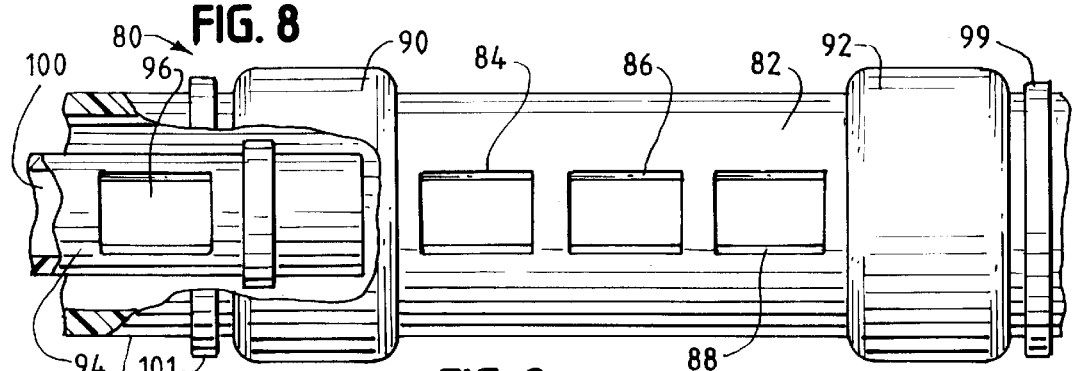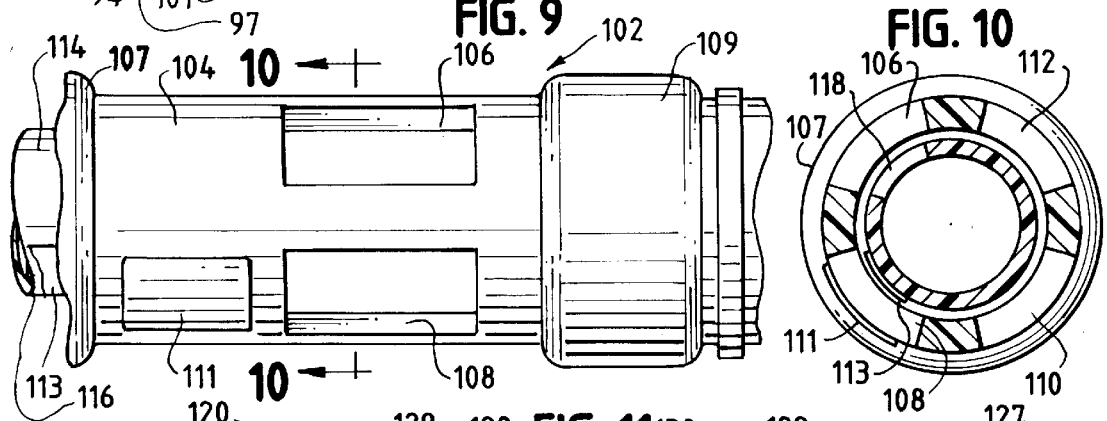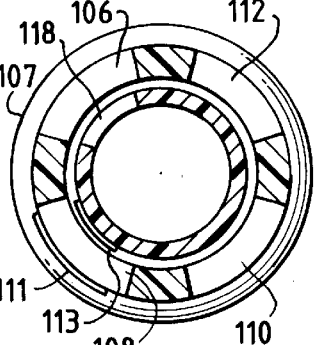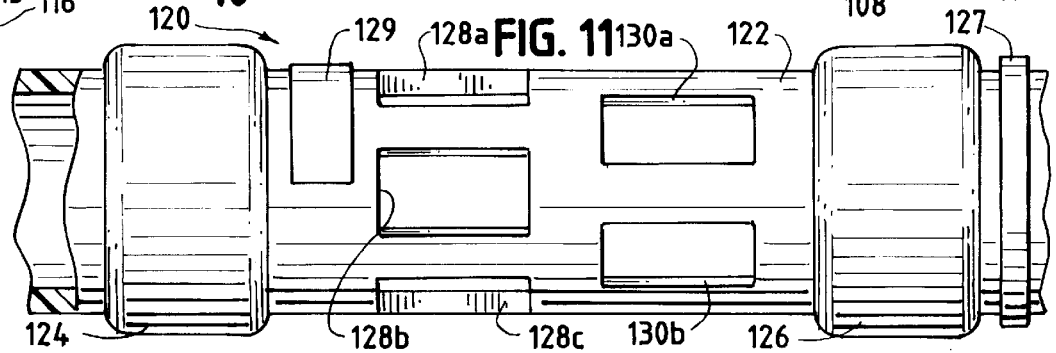

5,911,725

INTRALUMINAL RETRIEVAL CATHETER

BACKGROUND OF THE INVENTION

The present invention relates to body insertable medical devices, and more particularly to catheters for retrieving and removing unwanted objects from blood vessels and other body lumens.

A wide variety of treatment and diagnostic procedures involve the use of devices inserted into the body of a patient, either for temporary use or for permanent implantation. Among these devices are prostheses or stents of the radially self-expanding and plastically expandable types, grafts, combination stent/grafts, braided occlusion devices and embolization coils. Typically these devices are delivered endovascularly on catheters, to be released at the intended treatment site. Many of these devices are small and fragile. Further, because they cannot be viewed directly during deployment, radiopaque fluids, markers and other aids are used to assist transluminal delivery, initial positioning, release of the device, confirmation of position after release, and perhaps a repositioning if an initial positioning is not correct. Further steps, e.g. expanding the device through inflating a balloon, may be required.

In short, deployment of body insertable devices requires considerable skill and involves multiple stages, each involving a risk of the device releasing prematurely or breaking loose to become an unwanted foreign object in the vessel. The need to recover an insertable device might arise due to a fault in the insertable device, improper selection (e.g. wrong type or size), a fault in the deployment device, or improper technique. As the use of body insertable devices increases, so does this risk.

One known approach to retrieving or recovering such devices is disclosed in U.S. Pat. No. 5,171,233 (Amplatz et al). An intravascular snare includes an elongate catheter, with a loop-shaped segment of a wire extending from a distal end of the catheter, oriented at an angle of 45 degrees or more from the axial direction. The loop or snare can be formed of a superelastic shape memory alloy, so that it can be collapsed for intravascular delivery and opens into an unrestrained configuration upon emerging from the distal tip of the catheter. While a device of this type is capable of recovering insertable devices and other unwanted foreign matter, it also involves the risk of dislodging an object before it has been securely grasped. Then, blood flow may carry the object downstream into a narrower, more tortuous portion of the vessel, increasing the difficulty of recovery, and in some cases rendering recovery impossible without major surgery.

Therefore, it is an object of the present invention to provide an intraluminal retrieval device capable of retrieving a foreign object from a body lumen, with virtually no risk of the object becoming prematurely dislodged and carried out of reach by the flow of blood or another fluid.

Another object is to provide a retrieval device with a lumen isolation structure to confine an object for retrieval, while also more positively securing the retrieval device at a desired position along the body lumen.

A further object is to provide an intraluminal retrieval device that facilitates the use of aspiration and irrigation as effective options to snares or other coupling devices to remove objects from vasculature.

Yet another object is to provide a process for retrieving an object from a body lumen, in which the object is confined to a particular segment of the body lumen, before it is conveyed to a retrieval chamber for eventual removal from the body lumen.

SUMMARY OF THE INVENTION

To achieve these and other objects, there is provided an intraluminal retrieval apparatus. The apparatus includes an elongate and flexible first catheter with a proximal end region and a distal end region. The catheter is body insertable to position the distal end region within a body lumen while the proximal region remains outside of the body. An inlet passage along the distal end region is adapted to admit objects into a retrieval cavity from outside of the first catheter. A body lumen isolation structure, mounted to the first catheter, includes first and second occluding elements spaced apart from one another on opposite sides of the inlet passage. The occluding elements are positionable on opposite sides of an object situated within the body lumen to confine the object to a segment of the body lumen between the occluding elements. A retrieval device is mounted with respect to the first catheter and adapted to retrieve the object by forming a coupling with the object and conveying the object from outside of the first catheter into the retrieval cavity through the inlet passage.

A preferred retrieval apparatus includes a closure means operable to open and close the inlet passage. One suitable closure means is an elongate and flexible second catheter, contained within a catheter lumen of the first catheter extending from the proximal end region to the distal end region. The first catheter advantageously is provided with several apertures. Then, a single aperture of the second catheter can be aligned with one of the apertures through the first catheter. The remaining, unaligned apertures in the first catheter remain closed.

Several advantages arise from this selective alignment option. One is that the inlet passage can be moved axially or circumferentially through movement of the second catheter alone, while the first catheter remains fixed within the body lumen. Another is the ability to change the size of the inlet passage by providing apertures through the first or outer catheter of different sizes generally smaller than the aperture through the second, inner catheter.

After retrieval, the first catheter can be proximally withdrawn to remove the retrieved object. When a second catheter is employed, it preferably is mounted removably within the first catheter lumen. This enables a proximal withdrawal of the second catheter and the object, while the first catheter remains in place for further procedures, perhaps involving deployment of a stent or other device.

Suitable occlusion elements are inflatable balloons mounted to the outer catheter. A single balloon inflation lumen can be fluid coupled to both of the balloons to cause a desired simultaneous inflation of the balloons to secure the catheter and entrap the foreign object.

By confining the object to a limited section of the artery or other body lumen, the occlusion elements virtually eliminate the risk of the object dislodging and flowing out of recovery range. The occlusion elements further facilitate any retrieval approach that involves generating a fluid flow, either alone or to augment a snare or other coupling device. More particularly, with the occlusion elements isolating the body lumen segment containing the object, a vacuum source can be coupled to draw fluid proximally away from the retrieval cavity, whereupon fluid flows from outside the catheter into the cavity and tends to carry the object to the cavity as well. Alternatively, irrigation fluid can be supplied to the body lumen segment outside of the catheter, while a path is provided for discharge of irrigation fluid proximally away from the retrieval cavity.

Regardless of how retrieval is effected, the closure of the inlet passage after retrieval prevents the retrieved object from escaping the retrieval chamber or cavity. This enhances retrieval by devices generating fluid flows and by snares or other coupling devices, because in each case the retrieving device is required only to convey the object into the retrieval chamber, not transluminally out of the body.

Further in accordance with the invention, there is provided a process for retrieving an object from a body lumen, including:

a. bodily inserting an elongate and flexible catheter to selectively position a distal end of the catheter within a distal end of the catheter within a body lumen, such that first and second occluding elements mounted on a catheter are on opposite sides of an object in the body lumen;

b. activating the occluding elements to positionally secure the catheter within the body lumen and confine the object to a segment of the body lumen between the occluding elements;

c. with the catheter secured, opening an inlet passage along the catheter between the occluding elements, then retrieving the object by conveying the object through the inlet passage to a retrieval cavity in the catheter; and closing the inlet passage to retain the retrieved object in the retrieval cavity.

Then, if desired, the occluding elements are deactivated to release the catheter, which then is proximally withdrawn to remove the retrieved object.

Thus in accordance with the present invention, the risk of objects in body lumens becoming dislodged during attempted retrieval and unrecoverable is virtually eliminated by a recovery device that effectively entraps the object within a limited lumen segment prior to retrieval. Prospects for successfully retrieving implantable devices are considerably enhanced, thus to create new opportunities for employing retrieval devices in situations where the risk of a difficult recovery might otherwise have discouraged their use.

Aside from retrieving body insertable devices, the catheter is well suited for retrieving other foreign objects and unwanted matter, e.g. blood clots.

IN THE DRAWINGS

For a further understanding of the above and other features and advantages, reference is made to the following detailed description and to the drawings, in which:

FIG. 7 is a schematic view illustrating an alternative approach to retrieving the coil;

FIG. 8 illustrates an alternative embodiment retrieval device featuring axially spaced apart windows in an outer catheter thereof;

FIGS. 9 and 10 illustrate another alternative embodiment retrieval device including an outer catheter with circumferentially spaced apart windows;

FIG. 11 illustrates a further alternative embodiment retrieval device including an outer catheter with a staggered arrangement of windows;

DETAILED DESCRIPTION OF THE PREFERRED EMBODIMENTS

Figure 1:
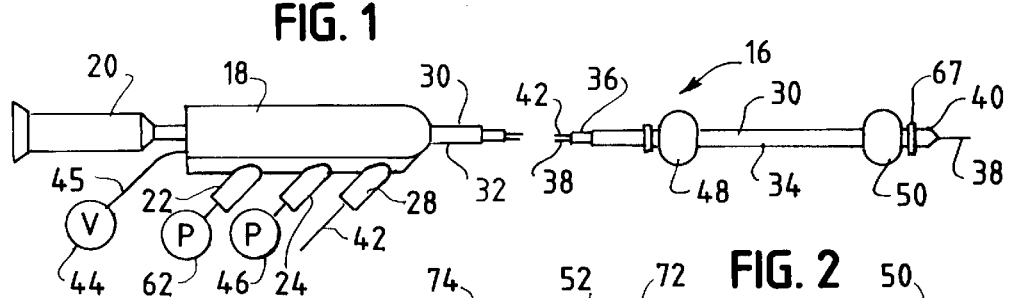
FIG. 1 is a side elevation of an intraluminal retrieval device constructed in accordance with the present invention.

Turning now to the drawings, there is shown in FIG. 1 an intraluminal retrieval device 16 used for retrieving foreign objects from arteries, veins and other body lumens. The device includes a control housing 18, a control handle 20, and several fittings extending from the housing as indicated at 22, 24, and 28. An outer catheter 30 includes a proximal end region 32 coupled to the housing, and a distal end region 34 remote from the housing. An inner catheter 36 is contained within outer catheter 30 and is rotatable and axially slidable relative to the outer catheter. Inner catheter 36 is operably coupled to control handle 20, so that the inner catheter can be rotated and moved axially relative to the outer catheter by manipulating the handle. The inner catheter extends distally to the distal end region of the outer catheter. Catheters 30 and 36 are constructed of biocompatible elastomers and have a favorable combination of axial stiffness and bending capability, in a manner known in the art, to enable the catheters to negotiate arteries and other internal body lumens. The outer surface of catheter 36 is contiguous with the inner surface of catheter 30. These catheters are shown spaced apart from one another in several figures, merely as a matter of convenience for illustrating certain features.

A guidewire 38, contained within inner catheter 36, extends distally beyond a distal tip 40 of catheter 30. Also contained within the inner catheter is a flexible wire 42 of a snare device. Wire 42 extends proximally from fitting 28, enabling a user to manipulate the snare device from the housing.

A vacuum source (pump) 44 is fluid coupled to the interior of catheter 36 through a line 45, and used to draw a vacuum and thereby cause a proximal fluid flow through the catheters. A positive pressure source (pump) 46 is coupled to fitting 24, and used to supply an irrigation fluid to the catheters.

In use, retrieval device is inserted, first by bodily inserting guidewire 38 and moving the guidewire transluminally to a predetermined treatment site. Then outer catheter 30 and inner catheter 36 are placed over a distal end of the guidewire, and pushed distally along the guidewire to bodily insert the catheters by their distal ends and push the catheters distally toward the intended retrieval site. When the catheters reach the retrieval site, the outer catheter is aligned to position a proximal balloon 48 and a distal balloon 50 on opposite sides of an object to be retrieved. Balloons 48 and 50, which are mounted to the outer catheter, then are expanded to secure outer catheter 30.

Figure 2:
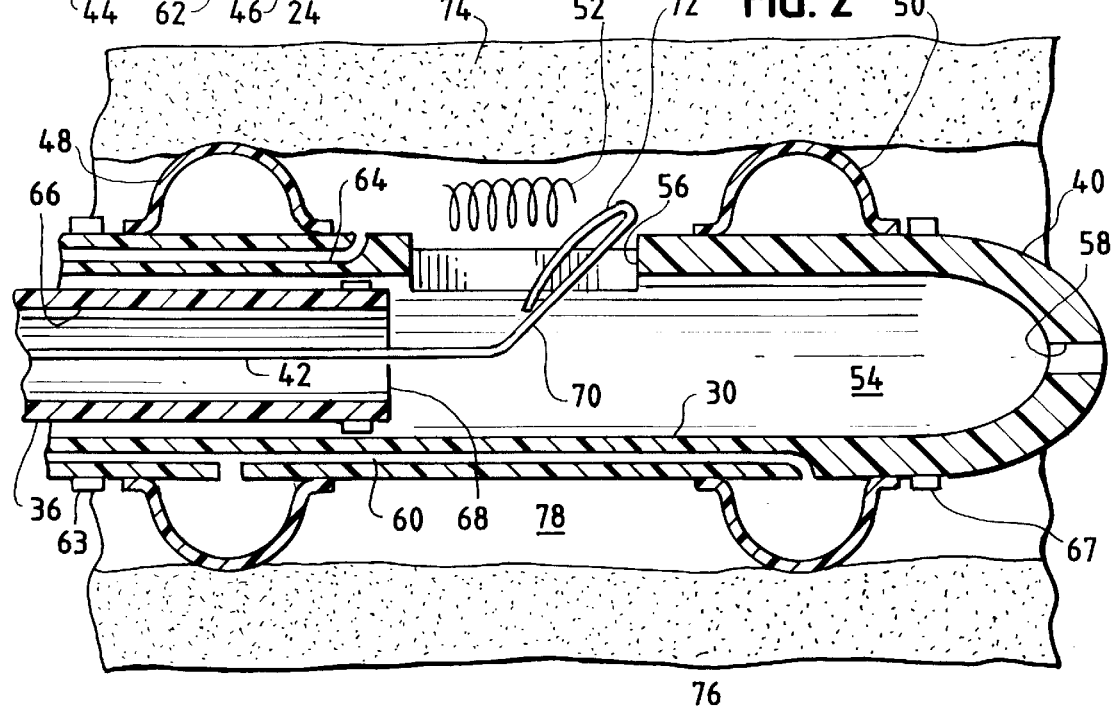
FIG. 2 is an enlarged sectioned elevation showing a distal end region of the device positioned within an artery to retrieve a coil from the artery.

For example, as shown in FIG. 2, the retrieval site is along an artery containing a coil 52. Distal end region 34 is shown in section to reveal a distal portion of a catheter lumen 54. Along the distal end region, lumen 54 provides a cavity or chamber for retrieved objects. An aperture or window 56, formed through the outer catheter between balloons 48 and 50, provides an inlet passage for admitting fluids and objects into the retrieval chamber from outside the catheter. A smaller distal tip opening 58 accommodates guidewire 38. Catheter lumen 54 further contains inner catheter 36 and thus extends proximally to the proximal end region of the outer catheter.

Two additional lumens are formed in the outer catheter and extend from the proximal end region to the distal end region. A balloon inflation lumen 60 is fluid coupled to fitting 22 to receive a balloon inflation fluid supplied under pressure from a source (pump) 62. Inflation lumen 60 is open to the interiors of balloons 48 and 50, so that the balloons are inflated simultaneously. Also, an irrigation lumen 64 is fluid coupled to fitting 24 to receive irrigation fluid from source 46. The irrigation lumen is open to the catheter exterior between balloons 48 and 50.

Inner catheter 36 has a catheter lumen 66 that extends proximally from a distal tip 68 of the inner catheter to a point within housing 18 where the lumen is fluid coupled to vacuum source 44 through line 45. Radiopaque markers 65 and 67 on the catheters near tips 40 and 68 respectively, and radiopaque markers 63 on catheter 30 near balloon 48, provide visibility for catheter positioning.

Wire 42 of snare device 70 is shown within lumen 66, except for a distal portion extending beyond the inner catheter. A coupling element is shown in the form of a loop 72, formed at the distal end of the flexible wire. Loop 72 is movable against coil 52 or another object, to form a coupling with the object. Then, wire 42 provides a transfer element to convey the loop and coupled object through window 56 into the retrieval chamber. Snare 70 can be formed in a manner similar to that described in U.S. Pat. No. 5,171,233 (Amplatz et al).

Suitable biocompatible polymers for constructing catheters 30 and 36 are known in the art, and include polyesters, polyolefins, polyamides and thermoplastic polyurethanes. Balloons 48 and 50 can be either distensible or non-distensible, and formed of materials such as polyethylene terepthalate (PET), nylons and polyolefins.

FIGS. 3–6 illustrate the use of device 16 to retrieve an object; more particularly, coil 52 lodged within an artery 74. The need has arisen to retrieve coil 52 and remove it from artery 74, perhaps because it was released prematurely from a deployment device, because it failed to expand properly upon release, or because it turned out to be the wrong size or type.

Figure 3:
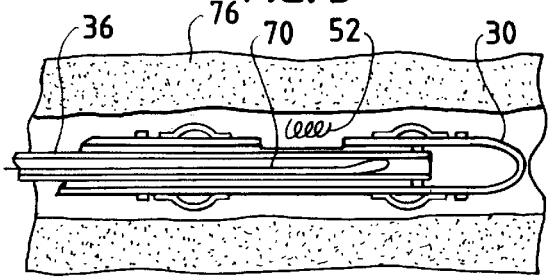
FIGS. 3–6 are schematic views illustrating retrieval of the coil.

In any event, the coil deployment device (not shown) is withdrawn and retrieval device 16 is inserted and advanced intravascularly as described above, until distal end region 34 is positioned as shown in FIG. 3, with balloons 48 and 50 on opposite sides of the coil. Inner catheter 36 is maintained in a position that keeps window 56 closed; i.e. with distal tip 68 of the catheter advanced distally beyond the window. Snare 70 is retained within the inner catheter.

With the device thus positioned, pump 62 is activated to supply a balloon inflation liquid, e.g. a saline solution, under pressure to balloon inflation lumen 60. Upon receiving the liquid, balloons 48 and 50 expand simultaneously and radially toward a surface engagement with an arterial wall 76. Surface engagement anchors or secures distal end region 34 within the artery, and further isolates an arterial segment 78 between balloons 48 and 50 from the remainder of artery 74.

Figure 4:
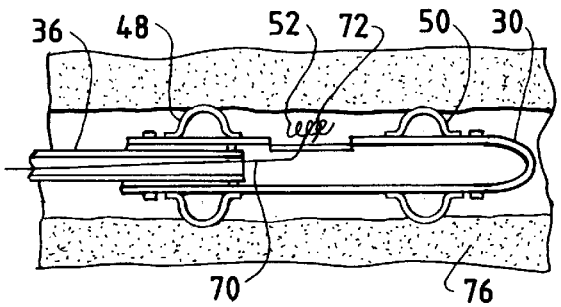

With outer catheter 30 fixed and with arterial segment 78 isolated, inner catheter 36 is moved proximally (using handle 20) to open window 56. Then, snare 70 is advanced distally within inner catheter 36, moving loop 72 out of the catheter and through window 56 to a point of engagement with coil 52 as shown in FIG. 4.

Successful retrieval depends on an effective coupling, which in this case is achieved by causing loop 72 to grasp coil 52. While such frequently is the case, there is a significant risk of unintentionally dislodging coil 52 from arterial wall 76 before the desired coupling is achieved. Using balloons 48 and 50 to isolate arterial segment 78 prevents premature dislodging from unduly interfering with successful retrieval and in some cases preventing retrieval altogether.

In the absence of balloons 48 and 50 or some other isolation structure, a prematurely dislodged coil or other object is taken downstream by the blood flow, at least temporarily beyond the reach of the retrieval device. The coil may come to rest in a constricted or tortuous portion of the artery, where retrieval is difficult or impossible without major surgery.

According to the present invention, this possibility is virtually eliminated. The isolation of arterial segment 78 interrupts blood flow, so that coil 52 even if prematurely dislodged is not likely to be carried beyond the reach of the retrieval device. Further, regardless of any tendency of the coil to drift, balloons 48 and 50 cooperate to confine the coil, preventing it from leaving arterial segment 78. The coil remains within reach of the retrieval device because it comes to rest within the isolated arterial segment, permitting further attempts to couple the coil and loop.

Figure 5:
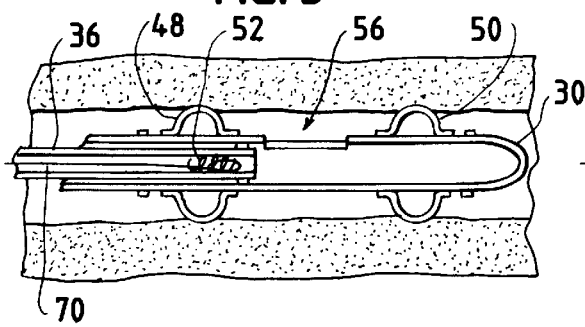
Figure 6:
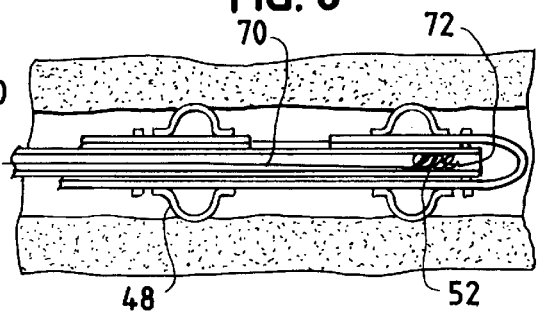

With the coupling established, snare wire 42 is pulled proximally from housing 18, to draw or convey loop 72 and coil 52 proximally into the inner catheter. The result is shown in FIG. 5. At this point, handle 20 is manipulated to move the inner catheter distally until it closes window 56 and secures coil 52 near distal tip 40 of the outer catheter, as seen in FIG. 6.

At this point, pump 62 can be activated for a reverse flow to aspirate balloons 48 and 50, freeing the outer catheter and inner catheter for withdrawal from the artery to remove the retrieved coil.

Alternatively, the balloons can remain expanded to secure the outer catheter, while inner catheter 36 and snare 70 are withdrawn to remove the coil.

In the sequence just described, catheter lumen 54 and catheter lumen 66 cooperate to provide the chamber for retaining coil 52. In a suitable alternative arrangement, inner catheter 36 need not be open at the distal tip, or alternatively can feature a minute opening sufficient to accommodate guidewire 38. In either case, the chamber would be provided solely by lumen 54 of the outer catheter. The coupled loop and coil would be drawn into lumen 54 through window 56, whereupon inner catheter 36 would be moved distally to close the window and push the loop and coil toward the outer catheter distal tip.

FIG. 7 illustrates several alternatives for retrieving a coil 52, without employing a snare. Both of the alternatives involve using balloons 48 and 50 to isolate arterial segment 78 as before. However, rather than advancing a snare to couple with the coil, the alternatives in FIG. 7 involve generating a liquid flow to convey coil 52 through window 56 and into the chamber.

One manner of generating the desired flow is to use vacuum source 44, coupled as shown in FIG. 1, to create a vacuum within lumen 66 of the inner catheter. The resulting proximal flow of liquid in lumen 66 draws liquid from outside of outer catheter 30, through window 56 and into the inner catheter lumen. Depending on the size of coil 52, the liquid flow carries the coil into inner catheter 36, or at least through the window into lumen 54 of the outer catheter. In either event, coil 52 is removed by proximal withdrawal, as before.

An alternative means to generate the desired liquid flow is through use of pump 46 to supply irrigation fluid to irrigation lumen 64, and then to arterial segment 78 outside of the outer catheter. With the inner catheter disposed proximally of window 56 as shown, the window and lumen 66 provide a discharge path for the irrigation fluid. Thus, the fluid flow again carries coil 52 into the inner catheter, or at least through window 56 into the chamber provided by the outer catheter. Of course, fluid flow can be enhanced if desired by simultaneous operation of pumps 44 and 46.

It is to be understood that the above description involving coil 52 notwithstanding, retrieval device 16 also can be used to recover other body insertable devices such as stents and stent grafts, and more generally can recover blood clots and other objects from vasculature and other body lumens. The distance between balloons 48 and 50, catheter diameters, and the dimensions of window 56 can be tailored to the object requiring retrieval. Stents, for example, can range in diameter from about 7–24 french (2.3–8 mm), and can range from several millimeters to about 40 mm in length. The appropriate retrieval device features thus vary over a similarly broad range.

FIG. 8 illustrates a distal end region of an alternative retrieval device 80 generally similar to retrieval device 16, but having an outer catheter 82 with three axially spaced apart windows 84, 86 and 88 situated between proximal and distal expandable balloons 90 and 92. Outer catheter 82 has a lumen that accommodates an inner catheter 94 for axial movement within the outer catheter. An aperture 96 is formed through inner catheter 94, near its distal end 98. Aperture 96 has substantially the same size and shape as the windows. This enables a selective positioning of catheters 82 and 94, in which aperture 96 can be aligned with any one of the windows, to select one of three axial locations for admitting objects and fluids from outside of catheter 82 into an inner catheter lumen 100. Thus, for example, if an object being retrieved is near window 84, then becomes dislodged and drifts to a location near window 86, inner catheter 94 can be shifted axially to align aperture 96 for a more convenient retrieval. Further, inner catheter 94 can be mounted rotatably within outer catheter 82, enabling an angular shift of aperture 96 to close all three of the windows. Radiopaque markers 97 and 99 on outer catheter 82, and a radiopaque marker 101 on inner catheter 94, aid catheter positioning. A salient feature of this device is the ability to shift the location of an inlet passage to the retrieval chamber, while the outer catheter remains fixed.

A further alternative retrieval device 102, illustrated in part in FIG. 9, also permits shifting of the inlet passage. In this case, an outer catheter 104 has four windows 106, 108, 110 and 112 between balloons 107 and 109, circumferentially or angularly spaced apart from one another in 90 degree intervals. An inner catheter 114, contained within a lumen 116 of the outer catheter, has a single aperture 118 with a size and shape similar to that of each window. The inner catheter is rotatable within the outer catheter, to selectively align aperture 118 with any one of windows 106–112, thus to locate the inlet passage at the selected window while the remaining windows are closed.

If desired, inner catheter 114 also can be slidable axially to effectively reduce the axial dimension of the passage formed with the selected window, or to close all windows. A radiopaque marker 111 on outer catheter 104, and a radiopaque marker 113 on inner catheter 115, facilitate catheter positioning. These markers do not extend around the entire circumferences of their respective catheters, and therefore can indicate angular as well as axial positioning. A primary advantage of this device is that there is no need to angularly align an outer catheter window to achieve proximity to the coil or other object requiring retrieval. Given a proper axial alignment, the object will be reasonably close to one of the four windows, and the inner catheter is rotated to an alignment with the window nearest the object while the outer catheter remains fixed.

FIG. 11 illustrates the distal end region of another alternative embodiment retrieval device 120, in which an outer catheter 122 includes two circumferential tiers of windows, axially spaced apart and staggered relative to one another, disposed between proximal and distal balloons 124 and 126. Each tier includes four windows spaced circumferentially at 90 degree intervals, with windows 128a–c of the proximal tier and windows 130a and 130b of the second tier being visible in the figure. An inner catheter with a single slot, e.g. similar to catheter 114 in FIGS. 9 and 10, can be used to selectively align an aperture with any of the windows. Windows 128 and 130 together provide complete coverage of the outer catheter circumference. Radiopaque markers 127 and 129 facilitate positioning.

As a further refinement, windows 128 and 130 can be formed in a variety of different sizes and shapes. So long as each window is either substantially smaller than or approximately the same size as the inner catheter aperture, the window rather than the aperture determines the size and shape of the inlet passage formed by the aligned window and aperture. This facilitates use of the same retrieval device to recover objects of widely ranging sizes and shapes.

Figure 12:
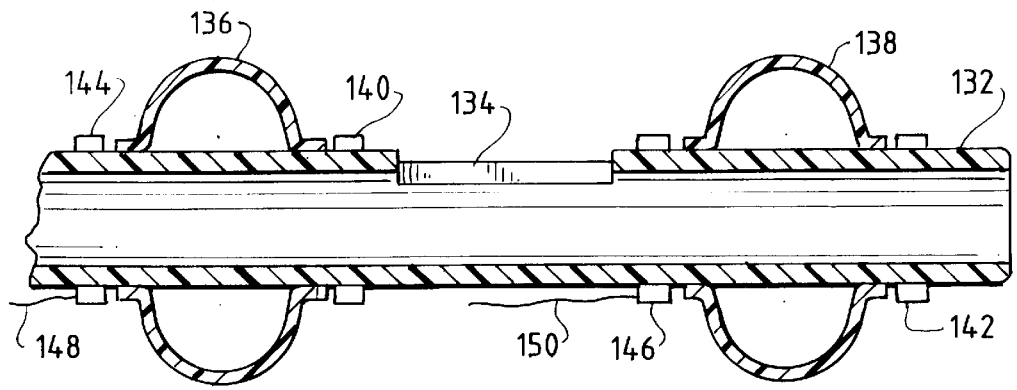
FIG. 12 illustrates another alternative embodiment retrieval device, with mesh structures to isolate part of a body lumen.

FIG. 12 shows the distal end of a retrieval catheter 132, open at its distal tip and having a retrieval opening 134. Mounted on opposite sides of the retrieval opening are proximal and distal mesh structures 136 and 138. Each mesh structure is fixed at its distal end, as indicated at 140 and 142, respectively. At its proximal end, proximal mesh structure 136 is secured to a ring 144. Mesh structure 138 is similarly secured to a ring 146. Rings 144 and 146 are mounted slidably on catheter 132, and controlled by wires 148 and 150, respectively, which extend to the proximal end of the catheter. The mesh structures can be normally biased toward an expanded state as shown, with wires 148 and 146 pulled proximally to flatten the mesh structures against the catheter. Thus, the mesh structures and wires are used in lieu of the dilatation balloons and dilatation fluid passages, for isolating an area from which the object is to be retrieved. Although not shown, an inner catheter with a slot positionable in alignment with opening 134 can be slidably contained within catheter 132, for controlled opening and closure of the retrieval opening as described above.

Retrieval devices according to the invention can be employed in narrow vessels, e.g. cranial vessels, by employing microcatheters and microballoons presently known for treating stenosis in cranial arteries. Typically a special guidewire would be employed, that would permit a threading of the microcatheter through the guidewire toward the intended treatment site.

Figure 13:
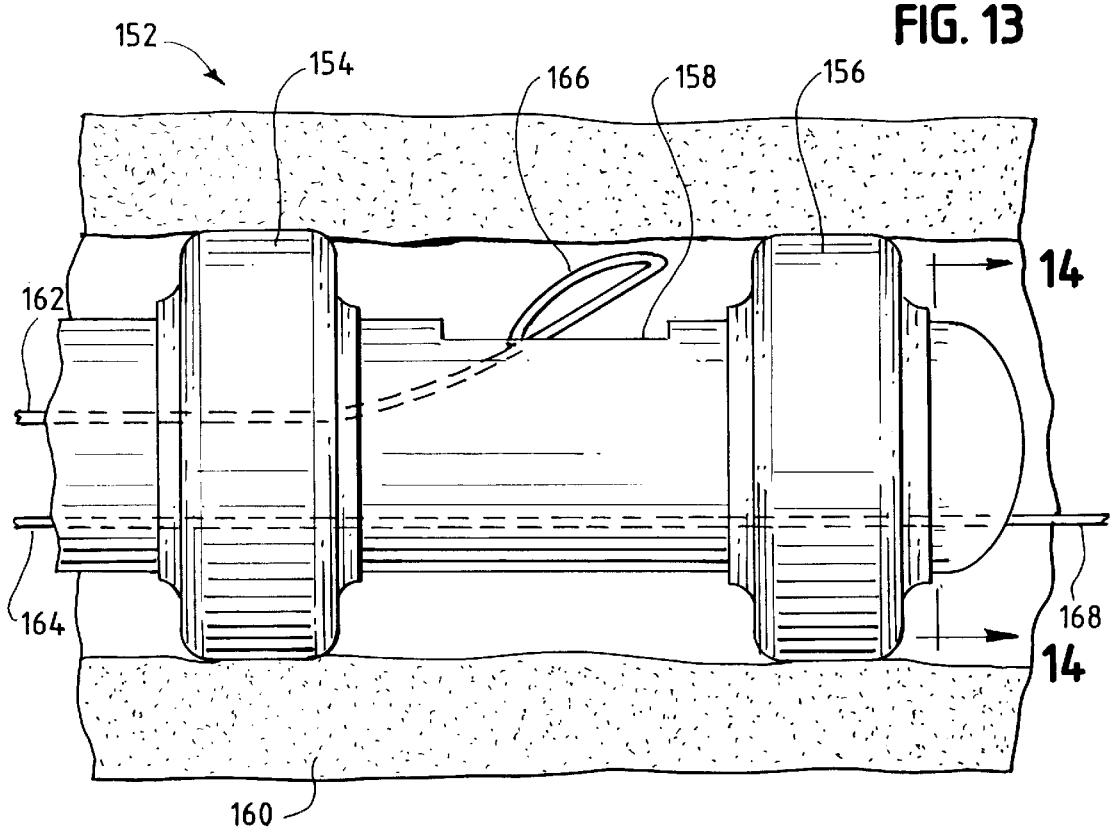
FIGS. 13 and 14 show another embodiment retrieval device adapted for intracranial applications.
Figure 14:
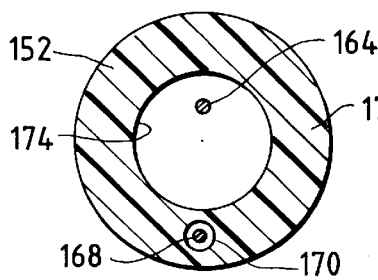

FIGS. 13 and 14 show a retrieval device in the form of a single catheter 152 designed for use in cranial vessels. There is no inner catheter contained within catheter 152. Consequently, catheter 152 can have a smaller diameter better suited to traverse the narrow vessels, e.g. three French or less. Proximal and distal microballoons, shown at 154 and 156 respectively, are mounted to the catheter on opposite sides of a retrieval opening 158. The balloons are shown expanded against the tissue wall of a cranial artery 160, thus to isolate an area of the artery surrounding opening 158. The catheter contains a snare 162, including a control wire 164 and a distal end loop 166 shown extending through the retrieval opening. The device incorporates a microguidewire 168 suited for cranial applications due to stiffness despite its small size, e.g. 9–10 mils in diameter. As best seen in FIG. 14, guidewire 168 is contained within a guidewire lumen 170 running through a wall 172 of catheter 152. Snare wire 164 is contained within a central lumen 174 of the catheter. While not illustrated, catheter 152 can be tapered if desired, i.e. converging to a smaller diameter in the distal direction.

In use, catheter 152 is introduced via the carotid artery to the cranial artery where a retrieval is intended. The microcatheter is advanced in the direction of blood flow, with flow aiding advancement. Typically, there is a point at which the microcatheter encounters resistance to further advancement. Then, guidewire 168 is advanced distally relative to catheter 152, along the artery and beyond the distal tip of the catheter. This is followed by distal movement of the catheter, over the guidewire and further along the artery.

When catheter 152 is advanced sufficiently to position balloons 154 and 156 on opposite sides of the object to be retrieved, the balloons are expanded to isolate the artery, and snare 162 advanced through the retrieval opening to retrieve the object.

Thus in accordance with the present invention, an intraluminal device can be used to retrieve objects with virtually no risk of the object becoming prematurely dislodged and carried to a location where retrieval is more difficult. The expandable balloons or other isolation structure positively secures the device, and effectively confines the object within a limited portion of the body lumen to prevent its escape. Such isolation not only reduces the risks involved in retrieval with snares or other coupling devices, but further enables retrieval by generating fluid flows, either by drawing a vacuum or providing a positive irrigation flow to the lumen surrounding the portion of the retrieval device adjacent the object.

I claim:

1. An intraluminal retrieval apparatus, including:

an elongate and flexible first catheter having a proximal end region and a distal end region, body insertable to position the distal end region within a body lumen while the proximal end region remains outside of the body;

means defining a retrieval cavity and an inlet passage along the distal end region adapted to admit objects into the retrieval cavity from outside of the first catheter;

a closure means for alternatively closing and opening the inlet passage;

a body lumen isolation structure mounted to the first catheter, including first and second isolating elements spaced apart from one another on opposite sides of the inlet passage, said isolating elements positionable on opposite sides of an object situated within the body lumen to confine the object to a segment of the body lumen between them; and a retrieval device mounted with respect to the first catheter and adapted to retrieve the object by forming a coupling with said object and conveying the object from outside of the first catheter into the cavity via the inlet passage.

2. The apparatus of claim 1 wherein:

said first catheter includes a first catheter lumen extending from the proximal end region to the distal end region, and the closure means comprises an elongate and flexible second catheter within the first catheter lumen and movable relative to the first catheter to alternatively open and close the inlet passage.

3. The apparatus of claim 2 wherein:

the retrieval cavity is formed in the second catheter;

the inlet passage comprises a plurality of first apertures through the first catheter open to the first catheter lumen, and a second aperture through the second catheter open to the retrieval cavity; and the second catheter is movable relative to the first catheter to alternatively align the second aperture with different selected ones of the first apertures.

4. The apparatus of claim 2 wherein:

the second catheter contains the retrieval cavity and is removably mounted within the first catheter, to enable removal of the retrieved object by withdrawing the second catheter proximally while the first catheter remains disposed within the body lumen.

5. The apparatus of claim 1 wherein:

said first catheter includes a catheter lumen extending along the catheter from the proximal end region to the distal end region and fluid coupled with the retrieval cavity, adapted for fluid coupling to a vacuum source for drawing fluids from outside of the catheter into the first catheter lumen via the inlet passage and retrieval cavity.

6. The apparatus of claim 1 wherein:

the isolating elements comprise first and second inflatable balloons, and a means for supplying a balloon inflation fluid under pressure to the balloons.

7. The apparatus of claim 6 wherein:

the supply means comprises a balloon inflation lumen open to interiors of the first and second balloons.

8. The apparatus of claim 1 wherein:

the retrieval device includes a snare adapted to form said coupling by grasping the object.

9. The apparatus of claim 8 wherein:

the first catheter includes a catheter lumen extending from the proximal end region to the distal end region, and the retrieval device further includes a flexible wire connected to the snare and extending proximally from the snare through the catheter lumen.

10. The apparatus of claim 1 wherein:

the first and second isolating elements cooperate to releasably fix the first catheter with respect to the body lumen.

11. An intraluminal retrieval apparatus, including:

an elongate and flexible first catheter having a proximal end region and a distal end region, body insertable to position the distal end region within a body lumen while the proximal end region remains outside of the body;

means defining a retrieval chamber and an inlet passage along the distal end region adapted to admit objects into the retrieval chamber from outside of the first catheter;

a body lumen isolation structure mounted to the first catheter and including first and second isolating elements spaced apart from one another on opposite sides of the inlet passage, said first and second isolating elements further positionable on opposite sides of an object within the body lumen to confine the object to a segment of the body lumen between them;

a closure means for alternatively opening the inlet passage to facilitate a flow of fluids into the chamber from outside of the catheter and closing the inlet passage to substantially prevent such flow; and an object retrieval component coupled to the first catheter and adapted to retrieve the object by conveying the object into the chamber via the inlet passage.

12. The apparatus of claim 11 wherein:

the first catheter includes a catheter lumen extending from the proximal region to the distal region, and the closure means comprises a second elongate and flexible catheter contained within the catheter lumen and movable to alternatively open and close the inlet passage.

13. The apparatus of claim 12 wherein:

the inlet passage comprises a plurality of first apertures through the first catheter, and a second aperture through the second catheter alternatively positionable in alignment with different selected ones of the first apertures to permit fluid flow through the selected first aperture and the second aperture into an interior of the second catheter, wherein the interior of the second catheter includes said chamber.

14. The apparatus of claim 12 wherein:

the isolating elements are adapted to fix the first catheter within the body lumen, and the second catheter is removably mounted within the first catheter to permit a proximal withdrawal of the second catheter and the retrieved object while the first catheter remains fixed within the body lumen.

15. The apparatus of claim 11 wherein:

the retrieval component comprises a retrieval device having a coupling element for forming a coupling with the object, and a transfer element joined to the coupling element and movable proximally to draw the coupling element and the object into the retrieval chamber.

16. The apparatus of claim 11 wherein:

the retrieval component comprises a vacuum source and a fluid pathway coupled between the retrieval chamber and the vacuum source, for generating a fluid flow to draw the object into the retrieval chamber via the inlet passage.

17. The apparatus of claim 16 wherein:

said fluid pathway comprises a first catheter lumen in the first catheter, extending from the retrieval chamber to the proximal end region.

18. The apparatus of claim 11 wherein:

the retrieval component comprises a supply path for supplying irrigation fluid to said segment of the body lumen outside of the first catheter, and a discharge path, including the retrieval chamber and the inlet passage, for removing irrigation fluid from said segment.

19. An intraluminal retrieval device, including:

an elongate and flexible first catheter having a proximal end region, a distal end region and a first catheter lumen extending from the proximal end region to the distal end region, said first catheter being body insertable to position the distal end region within a body lumen while the proximal end region remains outside of the body;

a plurality of first apertures formed through the first catheter and spaced apart from one another along the distal end region;

a lumen isolation structure mounted to the first catheter, including first and second isolating elements spaced apart from one another on opposite sides of the first apertures, said isolating elements positionable on opposite sides of an object in the body lumen to confine the object to a segment of the body lumen between them;

a second elongate and flexible catheter contained within said first catheter lumen and extending from the proximal end region to the distal end region, said second catheter including a second catheter lumen and a second aperture through the second catheter near a distal end thereof, the second catheter being movable relative to the first catheter to alternatively position the second aperture in alignment with selected different ones of the first apertures to admit a fluid flow from outside of the first catheter into the second catheter lumen via the selected first aperture and second aperture, and further alternatively movable to position the second aperture out of alignment with the first apertures to prevent such fluid flow; and a retrieval component, operable when the second aperture and the selected one of the first apertures are aligned, to retrieve the object by conveying an object from outside of the catheter into the second catheter lumen via the selected first aperture and second aperture.

20. The apparatus of claim 19 wherein:

the first apertures are spaced apart axially, and the second catheter is slidable axially relative to the first catheter to effect the alignment.

21. The apparatus of claim 19 wherein:

said first apertures are spaced apart circumferentially from one another, and the second catheter is rotatable within the first catheter lumen to effect the alignment.

22. The apparatus of claim 19 wherein:

the retrieval component comprises a retrieval device including a coupling element for forming a coupling with the object, and a transfer element joined to the coupling element and movable proximally to draw the coupling element and the object into the second catheter lumen.

23. The apparatus of claim 19 wherein:

the retrieval component comprises a vacuum source fluid coupled to the second catheter lumen, for generating a fluid flow to convey the object from said segment into the second catheter lumen.

24. The apparatus of claim 19 wherein:

the retrieval component comprises a supply path for supplying irrigation fluid to said segment of the body lumen outside of the first catheter, and a discharge path, including the selected first aperture, the second aperture and the second catheter lumen, for removing irrigation fluid from said segment.

25. A process for retrieving an object from a body lumen, including:

bodily inserting an elongate and flexible catheter to selectively position a distal end of the catheter within a body lumen such that first and second isolating elements mounted on the catheter are on opposite sides of an object in the body lumen;

activating the isolating elements to positionally fix the catheter within the body lumen and confine the object to a segment of the body lumen between the isolating elements;

with the catheter fixed, opening an inlet passage along the catheter between the isolating elements, then retrieving the object by conveying the object through the inlet passage to a retrieval cavity in the catheter; and closing the inlet passage to retain the retrieved object in the retrieval cavity.

26. The process of claim 25 further including:

deactivating the isolating elements to release the catheter, then proximally withdrawing the catheter to remove the retrieved object.

27. The process of claim 26 wherein:

the isolating elements comprise expandable balloons, and said activation and deactivation comprise, respectively, inflation and aspiration of the balloons.

28. The process of claim 25 wherein:

the retrieval of the object comprises moving a retrieval device from within the catheter toward the object to form a coupling therewith, then moving the retrieval device proximally to convey the object into the retrieval cavity.

29. The process of claim 25 wherein:

said retrieval comprises generating a fluid flow from outside of the catheter into the retrieval cavity through the inlet passage, thereby to convey the object into the retrieval cavity.

30. The process of claim 29 wherein:

the generating of the fluid flow comprises one of the following: (i) using a vacuum source to draw fluid proximally away from the retrieval cavity; and (ii) supplying irrigation fluid to a segment of the body lumen outside the catheter and between the isolating elements, and discharging the irrigation fluid proximally from the retrieval cavity.

* * * * *